United States Patent
Wang et al.

(10) Patent No.: US 9,392,993 B2
(45) Date of Patent: Jul. 19, 2016

(54) METHOD AND APPARATUS FOR ENHANCEMENT OF MEDICAL IMAGES

(71) Applicant: U-SYSTEMS, INC., Sunnyvale, CA (US)

(72) Inventors: Shih-Ping Wang, Los Altos, CA (US); Jiayu Chen, Palo Alto, CA (US); Hui Peng, Santa Clara, CA (US)

(73) Assignee: U-Systems, Inc., San Jose, CA (US)

( * ) Notice: Subject to any disclaimer, the term of this patent is extended or adjusted under 35 U.S.C. 154(b) by 618 days.

(21) Appl. No.: 13/648,040

(22) Filed: Oct. 9, 2012

(65) Prior Publication Data

US 2013/0253324 A1     Sep. 26, 2013

Related U.S. Application Data

(63) Continuation of application No. 13/399,974, filed on Feb. 17, 2012, now abandoned, which is a continuation of application No. 11/821,601, filed on Jun. 25, 2007, now abandoned, which is a continuation-in-part of application No. 11/597,196, filed as application No. PCT/US2005/018316 on May 23, 2005, now abandoned.

(60) Provisional application No. 60/577,388, filed on Jun. 4, 2004.

(51) Int. Cl.
 *A61B 8/00* (2006.01)
 *A61B 8/08* (2006.01)

(52) U.S. Cl.
 CPC .............. *A61B 8/0825* (2013.01); *A61B 8/406* (2013.01); *A61B 8/4218* (2013.01); *A61B 8/483* (2013.01); *A61B 8/54* (2013.01); *A61B 8/4281* (2013.01)

(58) Field of Classification Search
 CPC .............................. A61B 8/0825; A61B 8/406
 See application file for complete search history.

(56) References Cited

U.S. PATENT DOCUMENTS 4,545,385 A * 10/1985 Pirschel ........................ 600/445
6,117,081 A    9/2000 Jago et al.

(Continued)

FOREIGN PATENT DOCUMENTS

WO    WO 2004/030523 A2    4/2004
WO    WO 2005/104729 A2    11/2005

(Continued)

*Primary Examiner* — Amanda Lauritzen Moher
*Assistant Examiner* — Shahdeep Mohammed
(74) *Attorney, Agent, or Firm* — Alleman Hall McCoy Russell & Tuttle LLP

(57) ABSTRACT

Method and related apparatuses are described for performing automated ultrasound mammography with reduced nipple shadow effects. The breast is compressed in a direction generally toward the chest wall of the patient with one side of a compressive member which is preferably a membrane. The breast is scanned with an ultrasonic transducer array positioned in acoustic communication with the other side of the membrane. Beamsteering is used. The signals from the beamsteered energy are combined to generate one or more compound images having a reduced nipple shadow effect. An acoustic couplant is preferably applied between the breast and the membrane. The images of the sub-nipple region are also preferably enhanced by making comparisons with reference areas of the breast in areas away from the nipple shadow effected area. The images are preferably displayed to a user, either automatically or upon receiving a preference from the user.

19 Claims, 7 Drawing Sheets

(56) References Cited

U.S. PATENT DOCUMENTS

| | | |
|---|---|---|
| 6,126,598 A | 10/2000 | Entrekin et al. |
| 6,126,599 A | 10/2000 | Jago et al. |
| 6,135,956 A | 10/2000 | Schmiesing et al. |
| 6,524,246 B1 | 2/2003 | Kelly et al. |
| 6,574,499 B1 | 6/2003 | Dines et al. |
| 7,850,613 B2 | 12/2010 | Stribling |
| 2003/0007598 A1 | 1/2003 | Wang et al. |
| 2003/0149364 A1 | 8/2003 | Kapur et al. |
| 2004/0127793 A1 | 7/2004 | Mendlein et al. |
| 2004/0225221 A1 | 11/2004 | Olsson |
| 2006/0173304 A1 | 8/2006 | Wang |

FOREIGN PATENT DOCUMENTS

| | | |
|---|---|---|
| WO | WO 2005/120357 A1 | 12/2005 |
| WO | WO 2006/035381 A1 | 4/2006 |
| WO | WO 2007/014292 A2 | 2/2007 |

\* cited by examiner

METHOD AND APPARATUS FOR ENHANCEMENT OF MEDICAL IMAGES

CROSS REFERENCE TO RELATED APPLICATIONS

This application is a continuation of U.S. application Ser. No. 13/399,974, filed Feb. 17, 2012, which in turn is a continuation of U.S. application Ser. No. 11/821,601, filed Jun. 25, 2007, now abandoned, which in turn is a continuation-in-part of U.S. application Ser. No. 11/597,196, filed Nov. 20, 2006, now abandoned, which is a §371 national stage entry of PCT International Application No. PCT/US05/18316, filed May 23, 2005, which claims the benefit of U.S. Provisional Application No. 60/577,388, filed Jun. 4, 2004, each of these applications also being incorporated by reference herein in their entireties.

FIELD

This patent specification relates to medical imaging. More particularly, this patent specification relates to ultrasound mammography imaging.

BACKGROUND

Volumetric ultrasound scanning of the breast has been proposed as a complementary modality for breast cancer screening as described, for example, in the commonly assigned US 2003/007598A1 published Jan. 9, 2003, which is incorporated by reference herein. The commonly assigned WO 2004/030523A2 published Apr. 15, 2004, which is incorporated by reference herein, describes a full-field breast ultrasound (FFBU) scanning apparatus that compresses a breast along planes such as the craniocaudal (CC) plane, the mediolateral oblique (MLO) plane, etc., and ultrasonically scans the breast. One side of an at least partially conformable, substantially taut membrane or film sheet compresses the breast. A transducer translation mechanism maintains an ultrasound transducer in contact with the other side of the film sheet while translating the ultrasound transducer thereacross to scan the breast.

Other FFBU scanning devices that compress the breast in other directions, such as in generally chestward or "head-on" directions, are described in one or more of the following commonly assigned applications, each of which is incorporated by reference herein: U.S. Ser. No. 60/565,698 filed Apr. 26, 2004; U.S. Ser. No. 60/577,078 filed Jun. 4, 2004; U.S. Ser. No. 60/629,007 filed Nov. 17, 2004; U.S. Ser. No. 60/702,202 filed Jul. 25, 2005; U.S. Ser. No. 60/713,322 filed Aug. 31, 2005; WO 2005/104729A2 published Nov. 10, 2005; and WO 2005/120357A1 published Dec. 22, 2005.

One inherent problem in chestward compression ultrasonic mammography scans is ultrasonic "shadowing" caused by the nipple onto the tissue behind the nipple. The nipple and areola have a higher tissue density and acoustic attenuation compared with the remaining breast tissue. In a chestward compression scan, the nipple and areola are directly in the path of the acoustic waves between the transducer elements and substantial portions of underlying breast tissue. Therefore, an acoustic "shadow" is cast onto the underlying breast tissue positioned directly behind the nipple area. This nipple shadow effect can make it more difficult to analyze the underlying tissues in the resultant mammographic images.

Nipple shadowing is often less of a problem for non-chestward ultrasonic imaging. For example, in the cranio-caudal scans and medio-lateral oblique scans, the nipple is often not in the pathway of substantial portions of other breast tissue. Examples of non-chestward ultrasonic mammography are WO 2006/035381 A1, and US 2003/0149364 A1.

Thus, it would be desirable to facilitate automated chestward ultrasound scanning of a breast tissue volume in a manner that alleviates or otherwise reduces the effects of nipple shadowing.

SUMMARY

A method is provided for performing automated ultrasound mammography with reduced nipple shadow effects. The method involves compressing the breast in a direction generally toward the chest wall of the patient with one side of a compressive member which is preferably a membrane. The breast is scanned with an ultrasonic transducer array positioned in acoustic communication with the other side of the membrane, thereby transmitting and receiving ultrasonic energy into and from the breast tissue at at least two beam angles. The signals from the received ultrasonic energy at the two beam angles are combined to generate one or more compound images having a reduced nipple shadow effect. An acoustic couplant is preferably applied between the breast and the membrane. The images of the sub-nipple region are also preferably enhanced by making comparisons with reference areas of the breast in areas away from the nipple shadow effected area. The images are preferably displayed to a user, either automatically or upon receiving a preference from the user.

A system is also proved for performing automated ultrasound mammography with reduced nipple shadow effects. The system includes a compressive member, preferably a membrane, which is dimensioned and positionable to compress the breast in a direction generally toward the chest wall of a patient. The system includes an ultrasonic transducer array positioned and arranged to be in acoustic communication with the membrane, and an electronic beamformer in communication with the transducer array having electronics which can cause the transducer array to transmit ultrasound energy in a beam having a first angle and a beam having a second angle into the compressed breast. An image processing system combines the reflected signals from the ultrasound energy transmitted in the first and second angles such that the combined image has a reduced nipple shadow effect.

DETAILED DESCRIPTION

Figure 1:
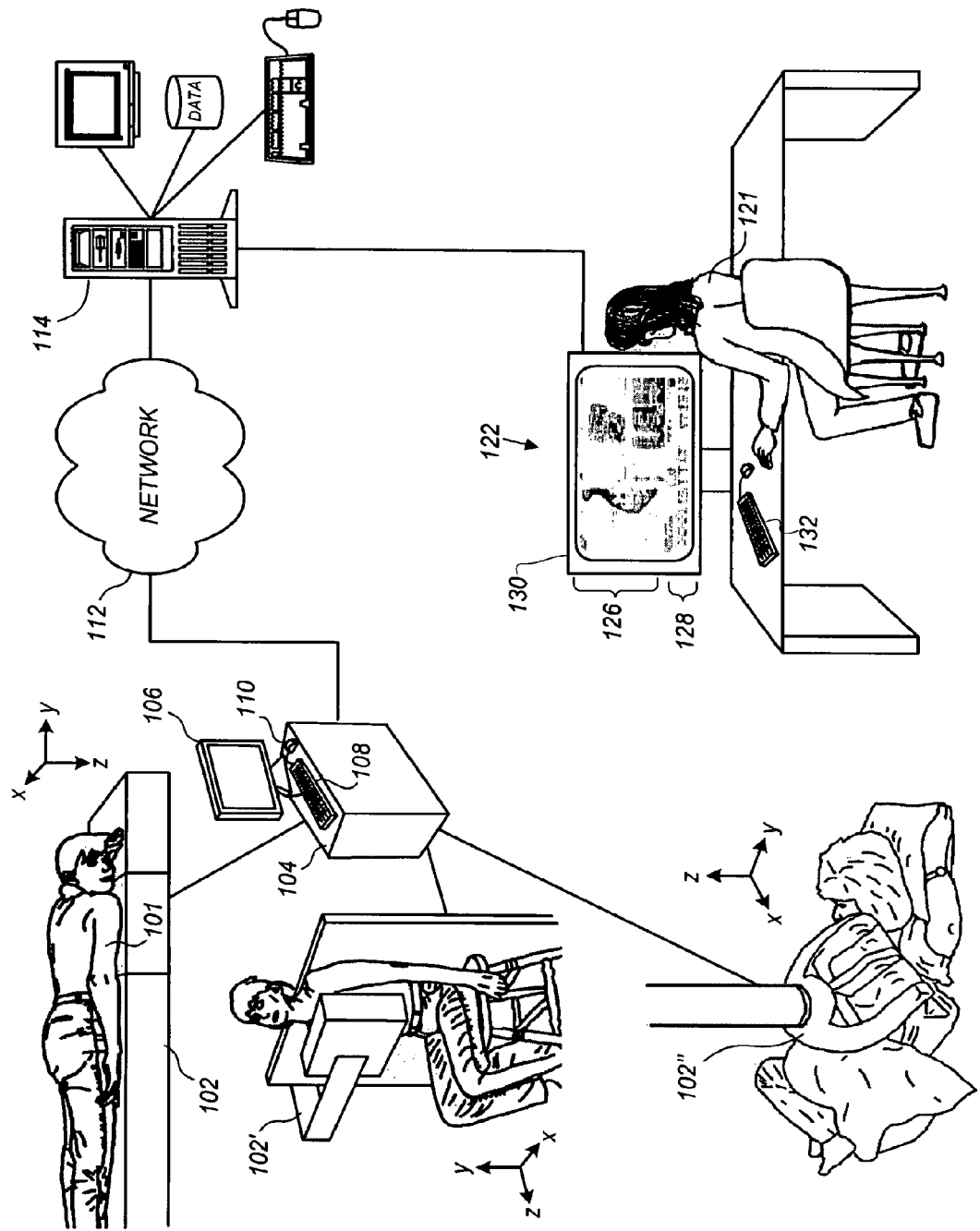
FIG. 1 illustrates a breast cancer screening and/or diagnosis system according to embodiments.

FIG. 1 illustrates a breast cancer screening and/or diagnosis system according to embodiments. The breast of a patient 101 is ultrasonically scanned by an automated scanning apparatus while the patient is in a prone position (device 102), an upright position (device 102'), a supine position (device 102") or other positions (not shown). By reducing the required ultrasonic penetration depth to the chest wall, scanning of a chestwardly compressed breast can occur at higher frequencies, e.g., 10-20 MHz, which can yield very high resolution images sufficient to facilitate detection of microcalcifications or other structures on the order of 1 mm near the chest wall.

Breast scans are obtained under the control of a scanning engine and workstation 104 including, for example, a monitor 106, keyboard 108, a mouse 110, and a scanning engine (not shown). During or after the scanning process, the ultrasound scan data is provided across a computer network 112 to an ultrasound server 114 that processes and generates display information according to the functionalities described herein. The ultrasound server 114 may perform other HIS/RIS (hospital information system/radiology information system) activities such as archiving, scheduling, etc. It is to be appreciated that the processing of the ultrasound scan data may be performed by any of a variety of different computing devices coupled to the computer network 112 in various combinations without departing from the scope of the preferred embodiments.

According to an embodiment, a viewing workstation 122 is provided that displays images to a clinician 121. As used herein, the term "clinician" generically refers to a medical professional, such as a radiologist, or other person that analyzes medical images and makes clinical determinations therefrom, it being understood that such person might be titled differently, or might have varying qualifications, depending on the country or locality of their particular medical environment. As used herein, the terms radiologist and physician are used interchangeably and generically to refer to medical professionals that analyze medical images and make clinical determinations therefrom, and/or that perform medical procedures under the at least partial guidance of medical imaging systems, it being understood that such person might be titled differently, or might have differing qualifications, depending on the country or locality of their particular medical environment. Viewing workstation 122 also includes user input devices 132 which ordinarily comprises a keyboard and mouse or other pointing device. The input devices 132 can also include a touch screen incorporated into display 130. High resolution display 130 is preferably used to display images and provide interactive feedback to clinician 121. Display 130 may consist of multiple monitors or a display unit. Shown on display 130 is image area 126 and a menu bar area 128. In another embodiment, viewing station 122 includes it own separate image processor and memory for processing and displaying in real time, images in response to input from clinician 121.

Figure 2:
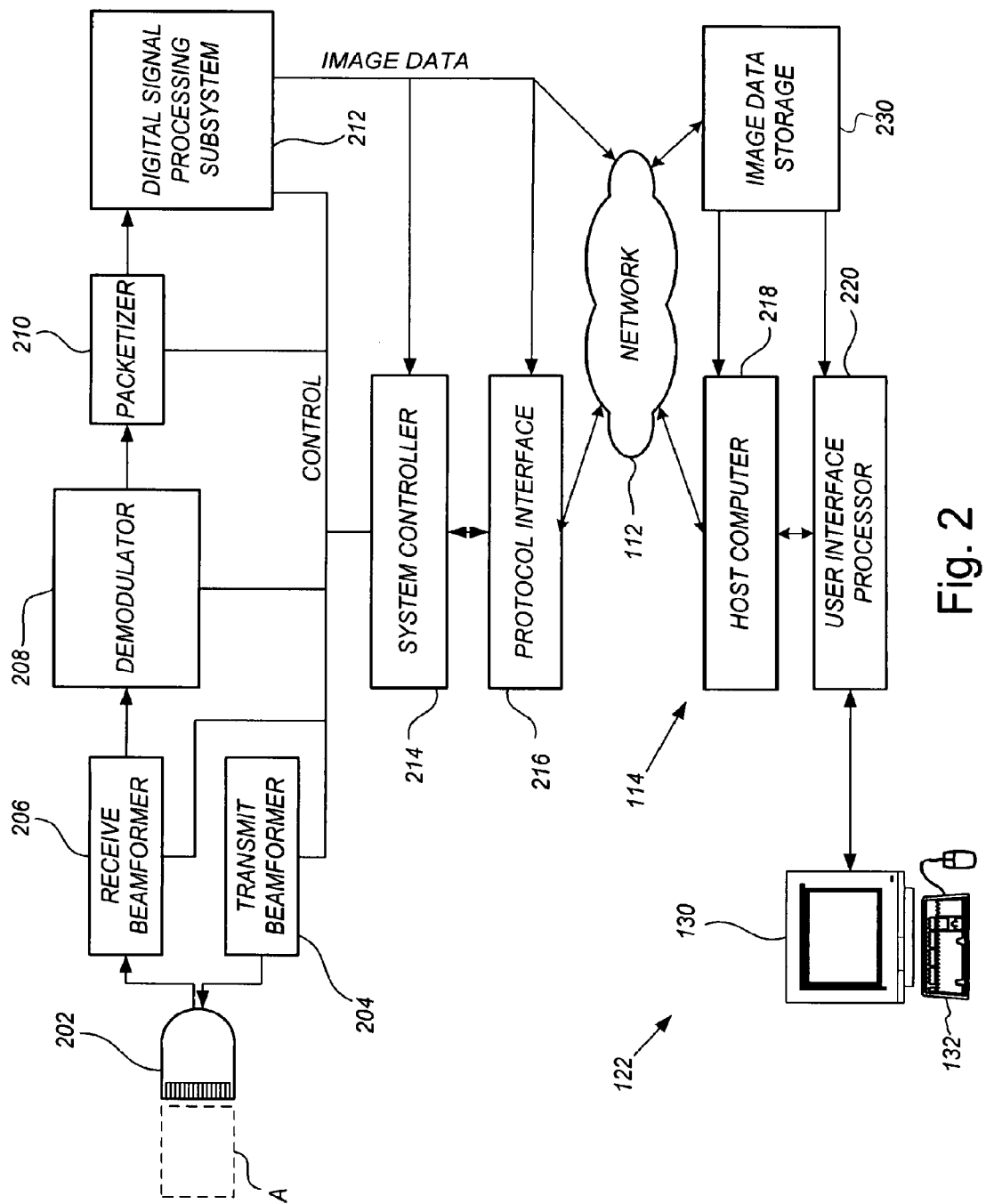
FIG. 2 illustrates a block diagram of components of an ultrasound imaging system in accordance with embodiments.
Figure 4:
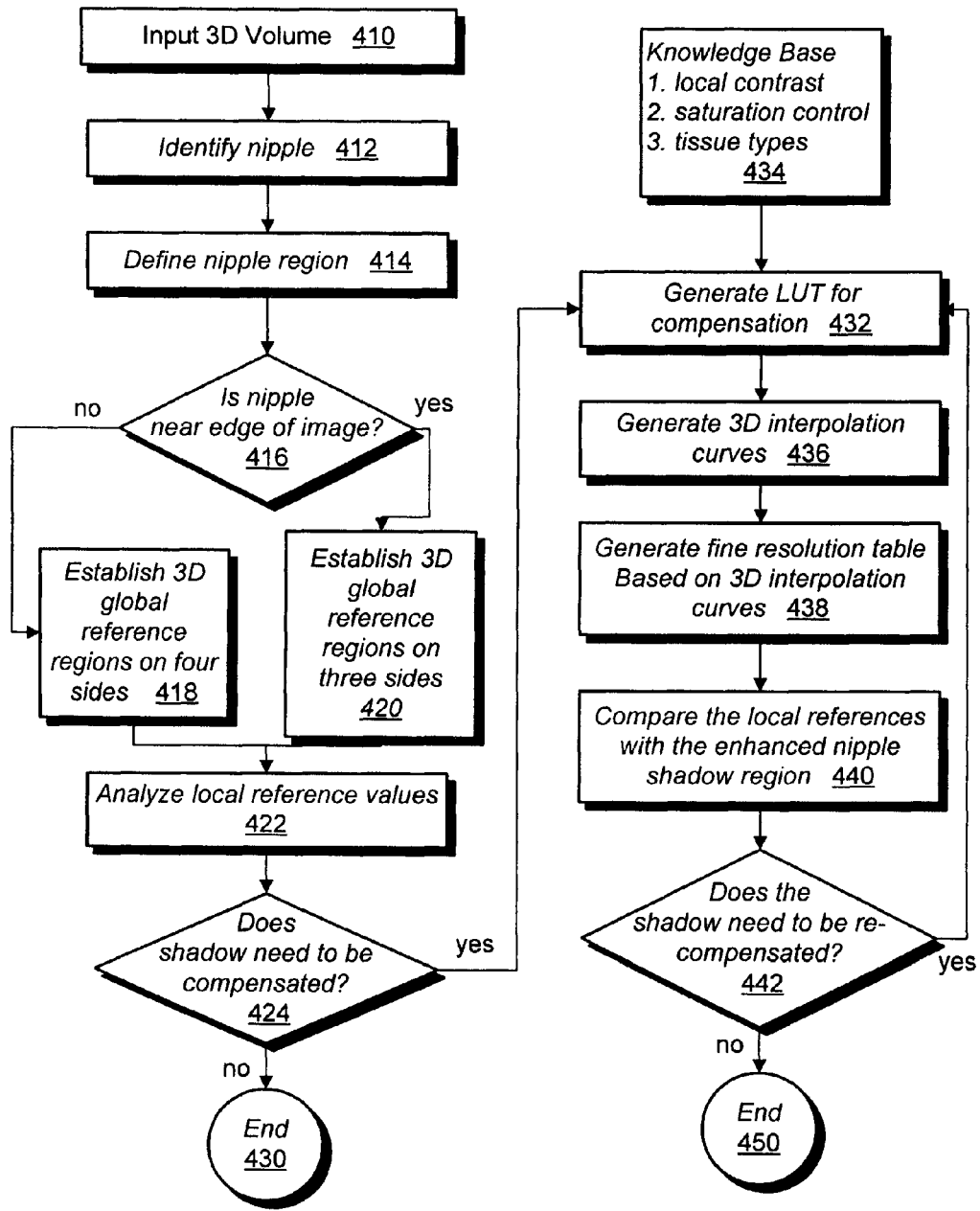
FIG. 4 illustrates steps in carrying out image enhancement techniques, according to embodiment.

FIG. 2 illustrates a block diagram of components of an ultrasound imaging system in accordance with embodiments. Transducer 202 comprises an array of transducer elements that transmits focused acoustic signals into a target responsive to signals generated by the transmit beamformer 204. In a preferred embodiment, transducer 202 transmits acoustic pulses into an area A that is fixed relative to the transducer. According to embodiments, angular beamsteering, in which component frames are taken at different angles relative to the transducer, is used. Responsive to control signals and parameters received from system controller 214, transmit beamformer 204 generates signals that are converted into acoustic interrogation signals by transducer 202 and introduced into the target human tissue A. Transducer 202 also receives acoustic echoes from the target and converts them into signals for forwarding to receive beamformer 206. Receive beamformer 206 receives the signals and converts them into a single-channel RF signal. Demodulator 208 receives the single-channel RF signal and generates component frames therefrom, which are then packetized by packetizer 210 and fed to DSP subsystem 212. In accordance with control signals and compounding weights received from system controller 214, DSP subsystem 212 is able to continuously generate compound output images by compounding component frames. The output image data is transferred to protocol interface 216, but may optionally be further processed by system controller 214. The compounded image data is transferred via network either to host computer 218, image data storage 230, or both. The image data is displayed to the user on display 130 via user interface processor 220. Further image enhancement to brighten areas of the nipple shadow area as described in FIG. 4, are preferably performed in host computer 218. Alternatively, the further image enhancement can be performed in a processor of viewing workstation 122.

According to an alternate embodiment, DSP subsystem 212 does not perform compounding of the image frames and the uncompounded image data is transferred directly to controller 214, protocol interface 216, and/or image data storage 230, optionally via network 112. The image frame data are then transferred via network 112 to host computer 218 which is preferably part of ultrasound server 114. Image data storage 230 is also preferably part of ultrasound server 114.

According to embodiments, image data storage 230 contains un-compounded image data. In response to user input received from input devices 132 in viewing station 122, the image data is processed by host computer 218 and displayed to the user at viewing station 122 via display 130. As described more fully below, if the user indicates a preference to view a particular original non-compounded image, the non-compounded images are displayed on display 130 in real time. If the user indicates a preference to view a compound image, host computer 218 compounds the image according to the user's preference and displays the compounded image on display 130 in real-time.

According to an alternative embodiment, as described above the image compounding can be performed by DSP subsystem 212 and stored on image data storage 230. In this embodiment, in the case when the user indicates a preference to view a compounded image, the host computer (or user interface processor directly) transfers and displays the appropriate stored compounded image.

According to a further alternative embodiment, host computer performs image enhancements as described with respect to FIG. 4 in one or more background processes and stores the enhanced image data on image data storage 230. In response to user input received from input devices 132 in viewing station 122, the image data in enhanced form or un-enhanced form is displayed to the user according to the user's preference.

Figure 3:
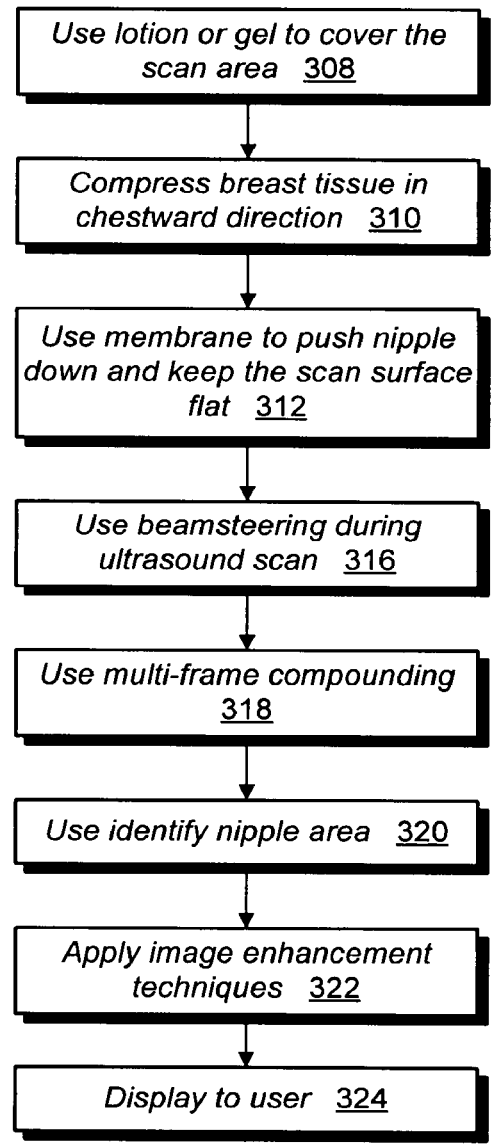
FIG. 3 illustrates steps in reducing the effects of nipples shadowing according to embodiments.

FIG. 3 illustrates steps in reducing the effects of nipples shadowing according to embodiments. In step 308, coupling lotion or coupling gel is applied to the breast including nipple area so as to cover the scan area during a chestward compression ultrasound scan. The lotion or gel should be of a nature to provide ultrasonic coupling between the transducer array and the tissue underlying the membrane. In step 310, the breast is compressed in a chestward direction. This could be done using ultrasound scanning devices such as devices 102, 102' and 102" as described in with respect to FIG. 1. Further details of scanning devices which could be used are described in commonly assigned PCT patent application entitled "Ultrasound Scanning And Ultrasound-Assisted Biopsy" filed on May 2, 2007, application No. PCT/US2007/010753, which is incorporated by reference herein. In step 312, a membrane is preferably used to push the nipple down and keep the scan surface flat. According to an embodiment the membrane is a taut fabric sheet that is preferably porous. In another embodiment, the membrane is a vented membrane. Further details of membranes suitable for use with these embodiments are provided in commonly-assigned PCT patent application no. WO 2007/014292 A2, filed on 25 Jul. 2006, which is incorporated by reference herein. The combination of the coupling gel or lotion and chestward compression with membrane reduces air bubbles and maintains a relatively flat scan surface over the nipple are of the breast during scanning.

In step 316, beamsteering is used during the ultrasound scanning to reduce the effects of nipple shadowing. The angle of beamsteering can be between about +/−5-30 degrees from perpendicular to the ultrasound array. It has been found that beamsteering angles of about +/−10 degrees is suitable for reducing the effects of nipple shadowing in many applications of chestward compression imaging. The scan rate can be between about 2 and 50 frames per second. It has been found that a scan rate of about 5 frames/sec is suitable for many applications. The scan speed is preferably about 0.6 mm per frame at the above recommended scan rates. It has been found that simple compounding of each pair of adjacent alternating beamsteered angle images greatly reduces the nipple shadow with chestward compression ultrasound scans. In step 318, multi-frame compounding is carried out. If the beamsteering angles are alternating between +/−10 degrees, then compounding each adjacent pair of frames will result in compounding a +10 degree and a −10 degree image. According to an alternate embodiment, more than two frames can be compounded to enhance the image. According to one example, 6 adjacent frames can be combined using compounding using weights such as from a Gaussian filter. One example of using such weights is as follows. Each pair of adjacent frames is compounded. Five of the compounded frames are then combined using weights such as: 20%, 60%, 100%, 60% and 20%, to produce a single frame weighted around the center two original frames.

Other examples of compounding component frames into a compound image include techniques using summations, averaging, peak detection, or other combinational means. Examples of spatial compounding from different angular viewpoints can be found in U.S. Pat. No. 6,117,081 (Jago et. al.), U.S. Pat. No. 6,126,598 (Entrekin et. al.), U.S. Pat. No. 6,126,599 (Jago et. al.), and U.S. Pat. No. 6,135,956 (Schmiesing et. al.), each of which are incorporated by reference herein. Other advantages of multi-angle compounding include reducing speckle effects and edge enhancements.

It has been found that significant improvement in the image directly beneath the nipple is achieved in many situations with the above described steps of beamsteering and compounding. However, in some cases the area beneath the nipple is still so dark so as to make analysis of the region difficult. According to further embodiments, further image enhancement techniques can be carried out. In step 320, the nipple area is identified. The nipple can be automatically detected using algorithms based on the attenuation contrast of the nipple area. However, it has been found that manual nipple marking is preferred in many situations.

In step 322, image enhancement techniques are applied. Increasing the brightness of shadow areas has been found to be useful in aiding the analysis of nipple shadow areas in some situations. The details of various embodiments for image enhancements are described with respect to FIG. 4 infra. In step 324, images of the breast volume are displayed to the user, such as a radiologist or other medical professional, on a viewing workstation such as workstation 122, shown and described with respect to FIG. 1 supra. The results of the beamsteering and compounding, and the subsequent image enhancements of the nipple shadow area can be displayed automatically as a default to the user, or can be selected "on" or "off" by the user. According to one embodiment, the beamsteering and compounding result is automatically displayed to the user and the additional image brightening enhancements described in FIG. 4 are optionally displayed to the user when the user clicks on an icon requesting the enhancement. According to a further embodiment, the image brightening enhancements are automatically displayed to the user and the effects of the enhancements are removed (i.e., the un-enhanced images are displayed) when the user clicks on an icon requesting that the image enhancements are turned "off". In order to increase the speed of display and usability of the viewing workstation, the image enhancement algorithms can be preformed automatically in the background so as to reduce the time needed to display the enhanced images when requested or by default.

FIG. 4 illustrates steps in carrying out image enhancement techniques, according to embodiment. In step 410, the 3D volume from the scanning process is input. The image is preferably the result of ultrasonic beamsteering and multi image compounding as described in above. In step 412, the nipple is identified. As mentioned above with respect to step 320 of FIG. 3, the nipple can be automatically or manually detected, although manual nipple marking is preferred in many situations. With manual nipple marking a human, typically the technician making the ultrasound scan, marks the center point of the nipple on a display screen using a mouse click, or other pointing device or user interface. Alternatively, the nipple can be marked later, during or before the analysis of the ultrasound scan information. Manual nipple marking has been found to be useful and efficient in many settings, since it is easily recognizable by humans, and reduces the risk of mis-identifying an abnormality as the nipple.

Figure 5A:
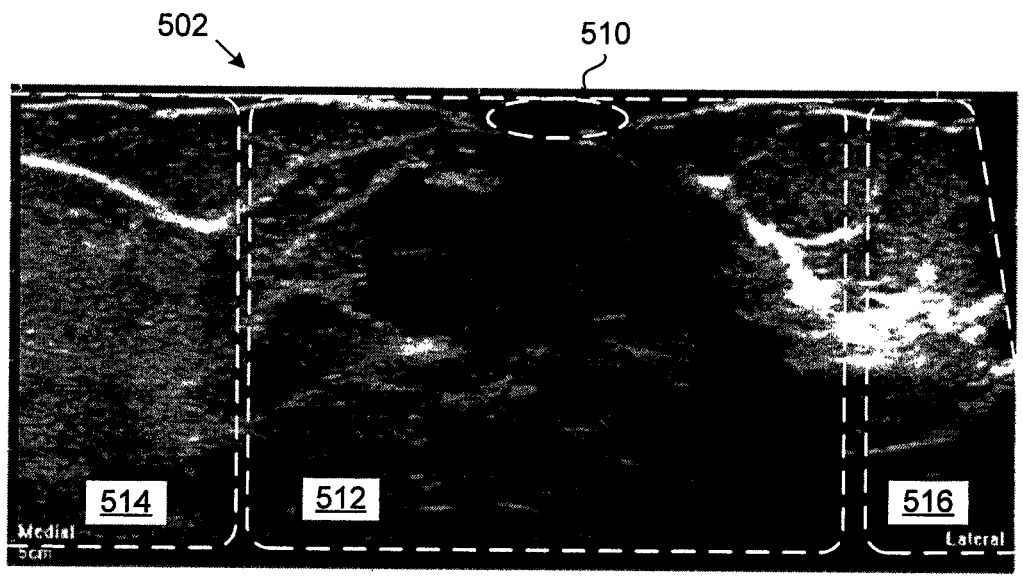
FIGS. 5a-b examples of images of ultrasonically scanned volumes of breast tissue according to embodiments.

In step 414, the nipple shadow region is defined. The nipple region is the volume of tissue beneath the nipple, or opposite the direction of the ultrasonic transducer, that is darker due to ultrasonic shadowing. In the case of a substantially chestward compression and imaging, the nipple region will be the volume of tissue towards the chest from the nipple. In practice it has been found that defining the nipple shadow region as a rectangular solid having x and z axis dimensions of about 2-8 cm is appropriate for many applications. Furthermore, a value of about 7 cm in the x direction and 6 cm in the z direction has been found to be appropriate for many applications. In the y axis direction, the nipple region should extend to the entire range of the imaged volume. Note that due to scanning rates, the image frame spacing in the z direction will not often allow for same dimensions in the x and z directions. In general, the nipple shadow region to be compensated should comfortably include most anticipated actual nipple shadows. It has been found that the actual ultrasonic shadow region is often about 4 cm in diameter, so the defined nipple shadow region of about 6-7 cm is typically appropriate. FIGS. 5a-b and 6a-b illustrate examples of images of ultrasonically scanned volumes of breast tissue according to embodiments. In FIG. 5a, image 502 shows nipple 510 and an example of defined nipple shadow region 512. In FIG. 6a, image 602 shows nipple 610 and an example of defined nipple shadow region 612.

Referring again to FIG. 4, in decision step 416, the image is analyzed to determine if the nipple is close to the edge of the image. In most cases of a chestward direction ultrasound scan, there will be more than one centimeter of imaged tissue on either side of the defined nipple shadow region. An example of such a case is shown in FIG. 5a. However, in some types of scans, such as a lateral scan or a medial scan the nipple will be more towards one side of the image, and there may not be more than one centimeter of imaged tissue on both sides of the defined nipple shadow region. FIG. 6a illustrates and example of an ultrasonic image 602 in which the defined nipple region 612 is close to the image edge 616. The nipple shadow region 612 is shown and is preferably defined as described in connection with step 414 above. Referring again to FIG. 4, if the edge of the nipple shadow area is 1 cm or less from the edge of the image, then control passes direction to step 420. If there is more than 1 cm of space between the defined nipple shadow region and the edge of the image, then control passes directly to step 418.

Figure 7:
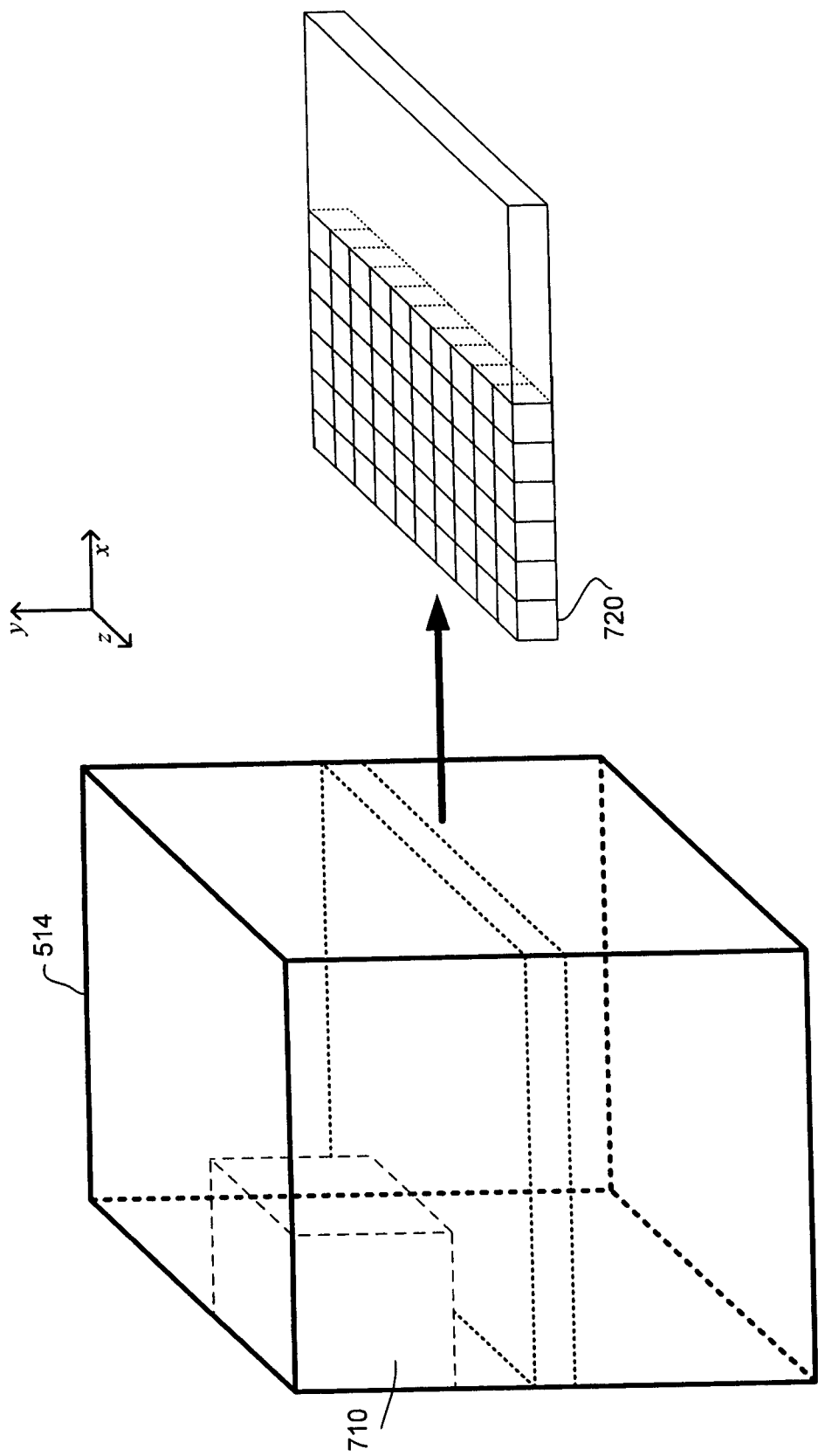
FIG. 7 illustrates and example of a reference region according to embodiments.

In step 418, a plurality of, preferably four, reference regions are established to determine an overall brightness level for the surrounding tissue. Various factors contribute to the apparent brightness of the final image viewed by a user, such as pixel value, monitor type, ambient light, gamma and contrast corrections. According to embodiments, pixel value is preferably used to evaluate brightness levels in various parts of the image space. As used herein the term "pixel" is used to include both 2D pixels and "voxels" or 3D pixels. It has been found that using three-dimensional reference volumes on each of the four sides of the rectangular nipple shadow region provides good image enhancement results in most cases. The three-dimensional reference volumes are preferably between about 6 cm and 8 cm wide in the x-direction, that is horizontally in the view of FIG. 5a, and include between about 6 cm and 8 cm of imaged tissue in the z-direction (in and out of the page in the view of FIG. 5a.). As in the case of the defined nipple shadow region, the reference regions use the entire tissue image in the y-direction. The overall brightness in terms of pixel value should preferably be established for different layers in the y-direction, since generally the tissue types, such as fatty tissues, etc, are layered horizontally. FIG. 7 illustrates and example of a reference region according to embodiments. To establish pixel value reference values, reference region 514 is first divided into large boxes, one of which is shown as box 710. It has been found that a large box dimension of about 2-3 cm on a side is suitable for a number of applications. It also has been found that the large boxes should overlap adjacent boxes by a substantial amount, for example 50%. A histogram and/or a gray level method is then applied to each large box. An average value for the histograms and/or a gray level is calculated for each horizontal layer of large boxes (that is, the large boxes having the same y-direction co-ordinates) to arrive at an overall brightness in terms of pixel value for the region at a certain y-value. The same process is carried out for the other three reference regions surrounding the nipple region. Reference region 516 in FIG. 5a is an example of one of these other three regions. Note that the other two regions will be displaced in the z-direction from the view shown in FIG. 5a. The overall brightness in terms of pixel value for the each y-value layer is then established by combining (e.g. averaging) the pixel values for each of the two reference regions. These brightness values are referred to as global reference values. According to yet another embodiment, the entire image volume can be treated as one large reference region and evaluated as described above, instead of defining three or four specific reference regions.

Referring again to FIG. 4, in step 420, the location of the boundary and rules relating the proximity to the boundary are added, and the 3D global reference values are established on only the remaining three sides of the nipple shadow region, since there is not enough useful space to define a reference region on the side of the nipple that is close to the edge. As in the case of step 418, the reference regions are preferably three-dimensional volumes between about 6 and 7 cms in both the x and z directions. An example of such a reference region is shown in FIG. 6a as reference region 614. As in the case of step 414, the reference region is divided into large boxes and a global reference value is established for each y-value. However, in the case of step 420 the global reference is only based on three reference regions instead of four.

Referring again to FIG. 4, in step 422, the local reference values are determined. Each reference region is divided into smaller boxes, one of which is shown as box 720 of FIG. 7. It has been found that the smaller boxes having dimensions of about 0.1 to 1.0 cm on a side is suitable for many applications. For many applications, it has been found that a small box side dimension of about 0.4 cm is suitable. Although the boxes, e.g. box 720, are shown in FIG. 7 as not overlapping, it has been found that each box overlapping adjacent boxes by about 20% yields good results in many cases. The smaller boxes having the same y-direction co-ordinates for midpoints are then averaged to determine a local brightness in terms of pixel value for each y-value. These brightness values are referred to as local reference values for each y-value. Note that in cases where the nipple region is not close to the image edge, then the local pixel values will be based on small box values from four reference regions, and in cases where the nipple region is close to the image edge, the local brightness values are based on small box value from the three reference regions. According to an embodiment, neither the large boxes, e.g. 710, nor the small boxes, e.g. 720, are used in analyzing the reference regions. Instead, the entire region is divided into a number of layers along the y-direction. That is, each layer has the same y-value coordinate ranges. The number of layers can range from very many, e.g. half the number of pixels in the y-direction, to a single layer. However, about 3-8 layers, and preferably 5 layers has been found to be suitable for many applications. The layers can overlap by about 20%. According to this embodiment, the simple average, or median value of the pixels values in the layers are used as reference values. In the case where there is only a single layer, the number of small boxes inside of the nipple compensation region may be more than one. According to an embodiment, a monotonically decreasing curve is used to simulate ultrasound gain attenuation with the increase of depth (y-value). By multiplying the reference value with the mono-decreasing curve, an estimate of how much the small boxes at each y-value depth needs to be compensated.

When combining the reference values for the plurality of reference regions (i.e. either three or four regions in the embodiments described above) a simple average can be used. However, it has been found that discarding the highest and lowest reference value and averaging the remaining values (in the case of four regions) yields suitable results in many cases.

According to other embodiments, the local reference value based on evaluations of brightness in the defined nipple shadow region instead of the reference regions. The nipple reference region is preferably defined so as to be larger than the actual nipple shadow area, so that it contains pixels with normal brightness as well as shadow areas. A nipple shadow region size of 6-7 cm is preferred in many applications. The nipple shadow region is then divided into small boxes as described above (0.1 to 1 cm, and 0.4 cm typical). The brightness of each small box is evaluated. The evaluation can be by averaging the pixel value, or can be by finding the median pixel value. A selection of relatively bright small boxes is then used in the local reference value. According to one embodiment, mean or median small box pixel values within a specific threshold band has been found to be useful in yielding good results. After calculating the brightness values (e.g. mean or median value) for each small box, the box brightness values are sorted by value. Only the values that are in a band from the brightest 10% to the brightest 5% are kept, and then averaged to obtain a single local reference value for each layer has the same y-value coordinate ranges (for example, for each of the 5 layers as described above). Note that through out this discussion of brightness enhancement, the methods to evaluate brightness of a box or regions of pixels includes both (1) calculating the mean pixel value, and (2) calculating the median pixel value. It is preferred that if one method (mean or median) is selected for one part of the algorithm, then the same method should be used elsewhere in evaluating brightness in areas or regions.

Referring again to FIG. 4, in decision step 424, an analysis is made to determine if shadow compensation is necessary. The defined nipple shadow region is preferably compared with the reference regions to determine if compensation or image enhancement is necessary. According to an embodiment, the nipple shadow region is divided into boxes in a similar or identical fashion as described with respect to the reference regions. An average nipple shadow region brightness in terms of pixel value is then calculated for each y-value which can then be compared to the corresponding global and/or local reference values to the same y-values. According to an embodiment, a simple threshold is used in which the nipple shadow region to reference pixel value ratios for each y-value are averaged into one average ratio or percentage. It has been found that a threshold of about 80% to 95% is suitable for many image analysis applications. That is, if the pixel value of the nipple shadow region is greater than 80% to 95% of the pixel value of the reference region(s) then no compensation is necessary. According to a further embodiment, a threshold of 90% is used to determine whether further compensation is necessary. If it is determined that no compensation is necessary, then the image enhancement process is ended in step 430. If it is determined that image compensation is useful, that is if the pixel value is below the threshold, then control passes to step 432.

In step 432, a look up table is generated to be used in compensating the nipple shadow region. The look up table is preferably based on the difference between the reference brightness in terms of pixel value and nipple shadow region brightness in terms of pixel values. Small boxes, of between 0.2 to 1.0 cm are preferably used, as described with respect to FIG. 7. The pixel values for each small box, preferably about 0.4 cm on a side and overlapping adjacent boxes by about 20% are averaged and then compared to the local reference values or layer average values from the reference regions. The difference in the pixel values between the small boxes in the nipple shadow region and the reference values are saved in the form of a look up table. A knowledge base 434 is preferably used to deal with certain types of situations. Specifically, it has been found that for effectiveness of image analysis, compensation should be applied to different bands of pixel values differently. To preserve local contrast in very dark areas, it has been found that below a pixel value of about $1/16^{th}$ the total pixel value range (e.g. pixel value 15 or below on a 0-255 pixel value range) no compensation should be used in the initial look up table. For very highly saturated areas, for example the brightest $1/8^{th}$ of the pixel value range (e.g. above about 220 on a 0-255 pixel value range) no compensation should be used in the initial look up table. For other pixel value ranges (i.e. neither very dark, nor very bright) the simple difference method has been found to be suitable in many situations. However, for other situations, one could divide the pixel value range into further bands and use other weighting or biasing for aid in image analysis. According to another embodiment, a weighting function is applied to both the reference values and the nipple shadow region to determine the reference values for use in calculating the look up table. In this embodiment, both the local reference values or reference layer values on the one hand and values from the nipple shadow region itself are combined in a weighted average before comparing to the small-box averages of the nipple shadow region to calculate the lookup table. It has been found that a weighting of 80% for the reference regions and 20% of the brightest parts (e.g. the highest 5-10%) of the nipple shadow region is suitable for many applications. The result of step 432 is preferably a look up table in which each centerpoint of each small box in the nipple shadow region is assigned a compensation value.

In step 436, three-dimensional interpolation curves are generated from the look up table. The goal in this step is to smooth the look up table so that the final image enhancement looks natural. It has been found that three-dimensional polynomial equations are suitable for smoothing the LUT in this step, however other type of smoothing (either linear or non-linear) may be used, depending on the particular application. The result of step 436 is preferably a smoothed table or set of curves being smoother than but having the same resolution as the look up table.

In step 438, a fine-resolution table is generated based on the three-dimensional interpolation curves, or otherwise smoothed LUT. In this step a pixel by pixel resolution adjustment curve is generated for the entire nipple shadow region according to the values in the three-dimensional interpolation curves. The result of applying the adjustment curve to the original pixel values is an image enhanced, or generally brightened, nipple shadow region. Step 438 can be done by saving a high-resolution table, that is having the same resolution as the original image, or it can be done on-the-fly using a pixel by pixel correction, which saves on storage resources. The 3D fine resolution table is preferably generated by applying three dimensional linear interpolation to the course curves generated in step 436. Bi-linear interpolation in the x-z or z-y plane can be performed first, followed by a linear interpolation in the third dimension. Finally, the generated fine resolution adjustment curve is used to adjust the pixel values of the nipple shadow region to yield the enhanced image.

In step 440, local reference is compared with the enhanced nipple shadow region to determine if further compensation would be beneficial. The comparison is preferably very similar or identical to that preformed in step 424, in which a small-box to small-box comparison and a simple threshold is used. It has been found that if the enhanced nipple region brightness is greater than 90% of the reference brightness, then the enhancement carried out was too strong. In this case, in step 442, the control passes back to step 432 for re-generation of the look up table. In the case where the compensation was too strong, then the LUT should be reduced by a factor, for example 10% in this iteration. In step 450, the image enhancement process is finished.

Figure 5B:
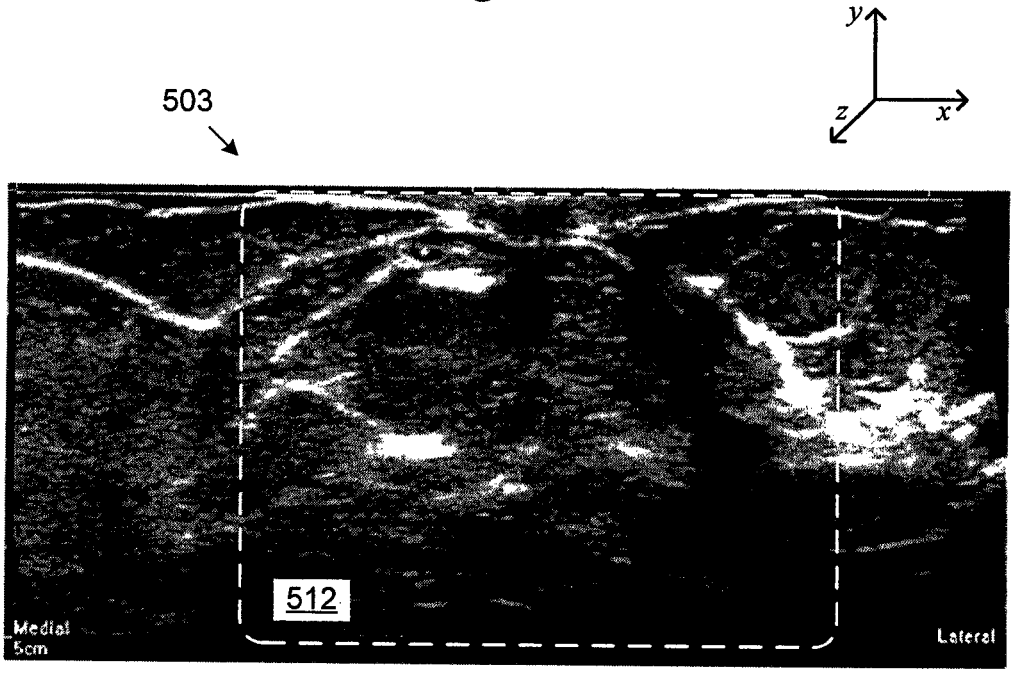
Figure 6A:
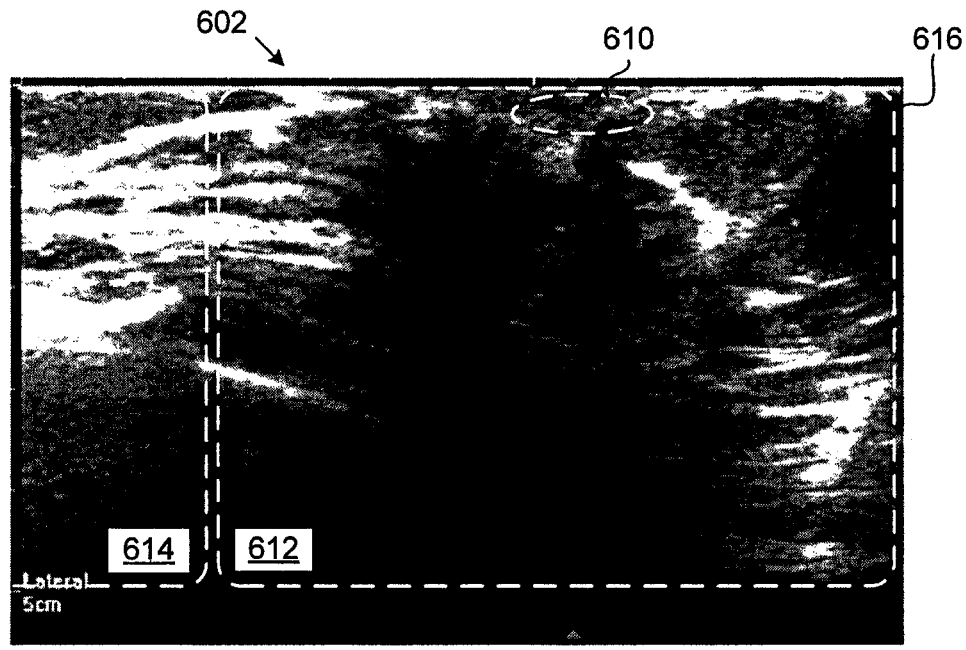
FIGS. 6a-b illustrate examples of images of ultrasonically scanned volumes of breast tissue according to embodiments.
Figure 6B:
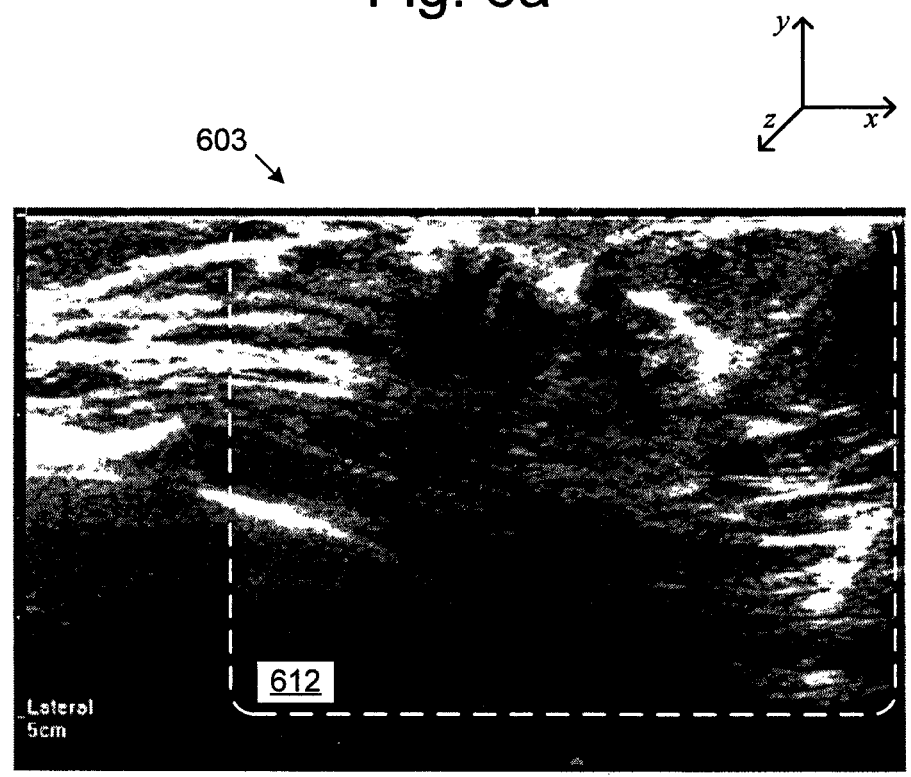

FIGS. 5b and 6b illustrate examples of enhanced nipple shadow regions 512 and 612 in images 503 and 603 respectively. Note that the shadow regions are enhanced in smooth and natural way such that the viewing clinician can make a useful and efficient analysis of the image including the enhanced nipple shadow area, without being distracted by image enhancement artifacts.

Whereas many alterations and modifications of the present invention will no doubt become apparent to a person of ordinary skill in the art after having read the foregoing description, it is to be understood that the particular embodiments shown and described by way of illustration are in no way intended to be considered limiting. For example, it has been found that image enhancement algorithms described in connection with FIG. 4 are also applicable to image enhancement in other known low signal areas such as the image edge areas. In the case of the image edge area, the beamsteered ultrasound energy can result in a weaker signal after simple compounding since only a fraction of the image frames (e.g. 50% in the case of alternating + and − beam steering angles) result form ultrasonic energy steered in the direction of the edge. The un-enhanced compound image will tend to look dark in the trapezoidal or triangular edge region. Weak signal areas can also result in the edge areas due to less contact pressure, not enough gel or lotion and or air bubbles. According to embodiments of the invention, the algorithms described in connection with FIG. 4, are used to enhance these edge regions. An edge region is defined instead of the nipple shadow region, and a single reference region is used as in the case where the nipple is close to the edge of the image. The edge region size will in general depend on the beamsteering angle and the size of the image. For a +/−10 degree beamsteering angle, a defined edge region of about 3 cm wide in the direction of the beamsteering, e.g. the x-direction, is suitable for many applications. The y and z direction dimensions can be the entire image size.

What is claimed is:

1. A method for performing automated ultrasound mammography with reduced nipple shadow effects comprising the steps of:
    compressing a breast in a direction toward a chest wall of a patient with a first side of a compressive member;
    said compressive member comprising a taut sheet of gel-wetted porous fabric contacting and compressing the breast with a first side of said gel-wetted fabric;
    scanning the breast with an ultrasonic transducer array positioned in acoustic communication with a second side of the gel-wetted fabric and contacting the gel-wetted fabric, thereby transmitting and receiving ultrasonic energy into and from the breast at a first beam angle and a second beam angle;
    combining signals from the received ultrasonic energy at said first and second beam angles to generate a compound image having reduced nipple shadow effects;
    identifying a nipple shadow region of the breast in the compound image that still displays nipple shadow effects; and
    carrying out additional enhancement of the compound image to further reduce nipple shadow effects by computer-processing, wherein a processor processes signals for additional enhancement of the image including the following signals:
        (i) signals from the received ultrasonic energy related to selected plural, spaced apart reference regions of the breast that are outside the nipple shadow region of the compound image to derive reference signals; and
        (ii) signals from the received ultrasonic energy of the nipple shadow region and said reference signals of the compound image.

2. The method of claim 1 in which said additional enhancement is configured to reduce nipple shadow effects by increasing brightness of the nipple shadow region in the compound image, and wherein said identifying comprises identifying the nipple shadow region that extends from a level of a nipple area of the breast to the patient's underlying chest wall automatically based on attenuation contrast of the nipple area.

3. The method of claim 1 in which said additional enhancement is configured to reduce nipple shadow effects by increasing brightness in the nipple shadow region only if and when said brightness meets a selected threshold relative to other brightness related to the breast.

4. The method of claim 1 in which said identifying comprises identifying a nipple shadow region that extends from a level of a nipple area of the breast to the patient's underlying chest wall based on user input.

5. The method of claim 1 wherein said computer-processing is configured to divide one or more of the reference regions into one or more pluralities of sub-regions and to evaluate brightness values in each of the plurality of sub-regions.

6. The method of claim 5 wherein said computer-processing is configured to divide the nipple shadow region into a plurality of sub-regions and to evaluate brightness values in each of the plurality of sub-regions of the nipple shadow region.

7. The method of claim 5 wherein said computer-processing further includes generating a compensation function for increasing the brightness of the nipple shadow region based at least in part on the evaluated brightness values in the one or more reference regions.

8. The method of claim 7 including storing the compensation function in computer memory as a look up table.

9. The method of claim 8 including smoothing values in the look up table in order to make the enhancement of the compound image look more natural to a user.

10. The method of claim 1 wherein the step of combining includes compounding two or more frames of data into a single frame of data.

11. The method of claim 1 wherein the step of combining includes compounding three or more frames of data into a single frame of data.

12. The method of claim 1 further comprising the step of selectively displaying one or more of (i) the compound image before said additional enhancement and (ii) the compound image after said additional enhancement.

13. The method of claim 12 including determining which of the images (i) and (ii) to display is based on user input regarding a user's preference for image enhancement.

14. A system for performing automated ultrasound mammography with reduced nipple shadow effects comprising:
    an ultrasonic scanning device comprising a taut sheet and dimensioned and configured to compress a breast in a direction toward a chest wall of a patient by contacting and compressing the breast with a first side of the taut sheet that is porous to an ultrasonic couplant;
    the ultrasonic scanning device further including an ultrasonic transducer array positioned in contact with and in acoustic communication with a second side of the taut, porous sheet;
    an electronic beamformer in communication with the transducer array, having electronics configured to cause the transducer array to transmit ultrasound energy into the compressed breast in a beam having a first angle and a beam having a second angle; and
    an image processing system comprising memory and a processor and arranged and programmed to generate breast images that are enhanced to reduce a nipple shadow effect by:
        (a) combining reflected signals from the ultrasound energy transmitted in the first and second angles to generate a compound image having reduced nipple shadow effect; and (b) computer-processing reflected signals of a selected nipple shadow region of the breast relative to reflected signals of plural reference regions that are in the patient's breast but are outside the nipple shadow region of the breast to generate the breast images with the reduced nipple shadow effect.

15. The system of claim 14 in which the taut, porous sheet is a sheet of woven fabric.

16. The system of claim 14 wherein the image processing system is configured to increase brightness of the nipple shadow region extending from a level of the nipple to a level of the patient's chest wall.

17. The system of claim 14 wherein the image processing system is configured to evaluate brightness values in each of the plural reference regions that are in the patient's breast but are outside the nipple shadow region of the breast.

18. The system of claim 17 wherein the image processing system is configured to divide the reference regions into a plurality of sub-regions and to evaluate brightness values in each of the plurality of sub-regions of the reference regions and to compare brightness of the reference regions with brightness of the nipple shadow region.

19. The system of claim 18 wherein the image processing system is configured to generate a compensation function for increasing brightness of the nipple shadow region based at least in part on the evaluated brightness values in said plural reference regions.

\* \* \* \* \*